US 7,935,379 B2

(12) United States Patent
Radhakrishnan et al.

(10) Patent No.: US 7,935,379 B2
(45) Date of Patent: May 3, 2011

(54) COATED AND IMPRINTED MEDICAL DEVICES AND METHODS OF MAKING THE SAME

(75) Inventors: Rajesh Radhakrishnan, Bothell, WA (US); Chandru Chandrasekaran, Mercer Island, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1271 days.

(21) Appl. No.: 11/274,792

(22) Filed: Nov. 14, 2005

(65) Prior Publication Data

US 2007/0110888 A1 May 17, 2007

(51) Int. Cl.
*B05D 3/12* (2006.01)
*A61L 33/00* (2006.01)

(52) U.S. Cl. ....... 427/2.1; 427/2.24; 427/2.25; 427/331; 427/335; 427/359; 427/261

(58) Field of Classification Search .......... 427/2.1–2.31, 427/256, 261
See application file for complete search history.

(56) References Cited

U.S. PATENT DOCUMENTS

| | | | | |
|---|---|---|---|---|
| 4,601,893 | A * | 7/1986 | Cardinal | 424/424 |
| 5,797,887 | A * | 8/1998 | Rosen et al. | 604/265 |
| 6,190,404 | B1 | 2/2001 | Palmaz et al. | |
| 6,274,294 | B1 | 8/2001 | Hines | |
| 6,451,373 | B1 * | 9/2002 | Hossainy et al. | 427/2.25 |
| 6,558,733 | B1 | 5/2003 | Hossainy et al. | |
| 6,904,658 | B2 | 6/2005 | Hines | |
| 2002/0050220 | A1 | 5/2002 | Schueller et al. | |
| 2004/0258914 | A1 * | 12/2004 | Chandra et al. | 428/375 |
| 2005/0090888 | A1 | 4/2005 | Hines et al. | |
| 2006/0171982 | A1 * | 8/2006 | Timm | 424/422 |

FOREIGN PATENT DOCUMENTS

| | | |
|---|---|---|
| DE | 197 24 871 A1 | 12/1997 |
| WO | WO 99/61261 | 12/1999 |
| WO | WO 02/26162 A2 | 4/2002 |
| WO | WO 03/023401 | 3/2003 |
| WO | WO 2005/000164 A1 | 1/2005 |

OTHER PUBLICATIONS

Xia et al. "Soft Lithography", *Annu. Rev. Mater. Sci.* vol. 28: pp. 153-184 (1998).
U.S. Appl. No. 11/274,793, filed Nov. 14, 2005, O'Brien.
International Search Report for International application No. PCT/US2006/043450.

* cited by examiner

*Primary Examiner* — Timothy H Meeks
*Assistant Examiner* — Cachet I Sellman
(74) *Attorney, Agent, or Firm* — Vidas, Arrett & Steinkraus, P.A.

(57) ABSTRACT

The present invention relates generally to coated medical devices, preferably a stent, that has a drug-eluting surface completely or partially coated with a coating that is imprinted with an impression. In particular, the invention is directed to a coated medical device having a coating that comprises biologically active materials, polymers, or a combination thereof. The coating is imprinted with an impression by printing, molding, lithography, or embossing techniques. Preferably, the patterning imprinted on the coating is capable of releasing biologically active materials in different amounts, at different rates, and/or at different time periods. The invention also relates to methods of making and methods of using the coated medical device.

18 Claims, 2 Drawing Sheets

COATED AND IMPRINTED MEDICAL DEVICES AND METHODS OF MAKING THE SAME

1. FIELD OF THE INVENTION

The present invention relates generally to coated medical devices, and methods for making such coated medical devices. In particular, the invention is directed to a medical device having a surface coated with a coating which is imprinted with an impression in order to increase the surface area of the coating. More particularly, the invention is directed to a medical device having a surface coated with a coating that comprises a biologically active material and/or polymer. Preferably, the biologically active material inhibits cell proliferation, contraction, migration, or hyperactivity (e.g., paclitaxel, an analog of paclitaxel, a derivative of paclitaxel, or a combination thereof) and/or has an immunosuppressant effect (e.g., sirolimus, everolimus, or tacrolimus). The medical device is capable of eluting the biologically active material, preferably, at two different rates depending on whether and how a section of the coating has been imprinted. The impression can be imprinted onto the coating, by printing, molding, lithography, or embossing techniques. Methods of using the coated medical device for treating restenosis in a subject, preferably a human, are also provided.

2. BACKGROUND OF THE INVENTION

Insertable or implantable coated medical devices have been used to treat a variety of medical conditions. For example, stents coated with drugs allow for the localized delivery of drugs into the body lumen. Drug-eluting stents have been used to prevent restenosis after balloon angioplasty. However, one of the difficulties in using drug-eluting medical devices is finding ways to control the release rate of the drug.

In the past, the rate of drug elution from a coated medical device has been controlled by manipulating the coating of the device (see U.S. Pat. No. 6,274,294 to Hines et al., U.S. Patent Publication No. US2002/0050220 to Schueller et al., and U.S. Patent Publication No. US2004/0237282 to Hines et al.), or by manipulating the composition of the device itself (see U.S. Patent Publication No. US2005/0090888 to Hines et al.). However, these approaches are limited in their use, especially where a single medical device is needed to elute drugs at different rates, or where a single medical device needs to target drugs at a particular body tissue. While multiple materials could be used to make a medical device that releases drugs at multiple rates, this method is economically inefficient.

Accordingly, there is a need for a more efficient method of delivering a biologically active material to a targeted body tissue. There is also a need for a method that releases a biologically active material at different rates. Furthermore, there is a need for a method that releases a biologically active material from only a certain portion of a medical device. There is also a need for a medical device made by such methods.

3. SUMMARY OF THE INVENTION

To achieve the aforementioned objectives, the inventor has invented insertable or implantable medical devices having a coating that is imprinted with an impression.

The invention relates generally to drug-eluting medical devices comprising a surface and a coating disposed on at least a portion of the surface, where an impression is imprinted on at least a region of the coating, in order to increase the surface area of the aforementioned coating. In certain embodiments, the coating of the medical device comprises a biologically active material. In other embodiments, the coating comprises a plurality of coating layers. In one embodiment, the biologically active material is dispersed in the coating. In a preferred embodiment, the biologically active material is uniformly dispersed in the coating. In a specific embodiment, the coating is capable of sustained release of the biologically active material over a period of time.

Preferably, the biologically active material inhibits cell proliferation, contraction, migration, or hyperactivity. In one embodiment, the biologically active material comprises an immunosuppressant, an antiproliferative agent, or a combination thereof. In a preferred embodiment, the biologically active material comprises an immunosuppressant such as sirolimus, everolimus, tacrolimus, or a combination thereof. In another preferred embodiment, the biologically active material comprises an antiproliferative agent such as paclitaxel, (i.e., paclitaxel, an analog of paclitaxel, a derivative of paclitaxel, or a combination thereof). In another preferred embodiment, the biologically active material inhibits activity of smooth muscle cells. In certain embodiments, the biologically active material does not comprise excipients.

In certain embodiments, when the medical device is in use, the biologically active material is released from the coating at a first rate that is different from a second rate, wherein the second rate is the rate of release of the same biologically active material from the coating had the impression not been imprinted on the coating.

In one embodiment, the release rate of a biologically active material from a medical device having an imprinted coating is greater than the release rate of the same biologically active material from a medical device having a non-imprinted coating. In another embodiment, the release rate of a biologically active material from a medical device having an imprinted coating is slower than the release rate of the same biologically active material from a medical device having a non-imprinted coating.

In certain embodiments, the coating of the medical device further comprises a polymer. The polymer can comprise, without limitation, one or more of the following polymers: styrene-isobutylene-styrene, polyurethanes, silicones, polyesters, polyolefins, polyisobutylene, ethylene-alphaolefin copolymers, acrylic polymers and copolymers, vinyl halide polymers, polyvinyl ethers, polyvinylidene halides, polyacrylonitrile, polyvinyl ketones, polyvinyl aromatics, polyvinyl esters, copolymers of vinyl monomers, copolymers of vinyl monomers and olefins, polyamides, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM rubbers, fluorosilicones, polyethylene glycol, polysaccharides, phospholipids, or a combination thereof.

The medical device is suitable for insertion or implantation into a subject, preferably a human. Preferably, the medical device is an intravascular stent. In one embodiment, the medical device is a metallic intravascular stent. In a specific embodiment, the medical device is a stainless steel intravascular stent. In other embodiments, the medical device is a vascular graft or coil such as a Guglielmi Detachable Coil (GDC).

The invention also relates to methods of making the coated medical device. In one embodiment, the method of making the coated medical device comprises providing a medical device that comprises a surface suitable for exposure to body tissue, disposing a coating on at least a portion of the surface to form a first surface area, and imprinting an impression on at least a region of the coating by a technique comprising molding, microcontact printing, inkjet printing, screen printing, or a combination thereof, to increase the first surface area.

In certain embodiments, the coating is disposed onto the medical device by spraying, dipping, direct deposition, or a combination thereof. In one embodiment, the coating comprises a biologically active material that inhibits cell proliferation, contraction, migration, or hyperactivity. In another embodiment, the coating comprises a biologically active material that inhibits an activity of a smooth muscle cell.

The invention also relates to methods of imprinting the impression on the coating of the medical device. In certain embodiments, the impression is imprinted on a region or throughout the coating of the medical device by a printing technique. In preferred embodiments, this printing technique is microcontact printing, inkjet printing, screen printing, or a combination thereof.

In certain embodiments, the impression is imprinted on a region of or throughout the coating of the medical device by a molding technique. In preferred embodiments, the coating may be imprinted with an impression using replica molding, microtransfer molding, micromolding in capillaries, solvent-assisted micromolding, or a combination thereof.

In certain embodiments, the impression is imprinted on a region of or throughout the coating of the medical device using a lithography technique. In preferred embodiments, the coating may be imprinted with an impression using scanning probe lithography, proximal probe lithography, photolithography, or a combination thereof.

In certain embodiments, the impression is imprinted on a region of or throughout the coating of the medical device using an embossing technique.

The invention further relates to methods for treating or preventing stenosis or restenosis or addressing other conditions (e.g., cancer) comprising inserting or implanting the medical device into a blood vessel of a subject in need thereof.

The invention also relates to methods of controlling the rate of endothelialization of the medical device to the neighbouring body tissue. In one embodiment, when the medical device is used, the rate of endothelialization to the body tissue may differ depending on whether the coating of the medical device has been imprinted and/or the extent of the impression. The medical device may be inserted or implanted alone or in combination with other treatment protocols.

4. FIGURES

FIG. 1A is a partial cross-sectional view of a coated medical device 3 before its coating 5 is imprinted by a dimethyl-siloxane (PDMS) mold 1.

FIG. 1B is a partial cross-sectional view of the coated medical device 3 of FIG. 1A after its coating 5 is impressed with an impression 6 by the PDMS mold 1.

Figure 1A:
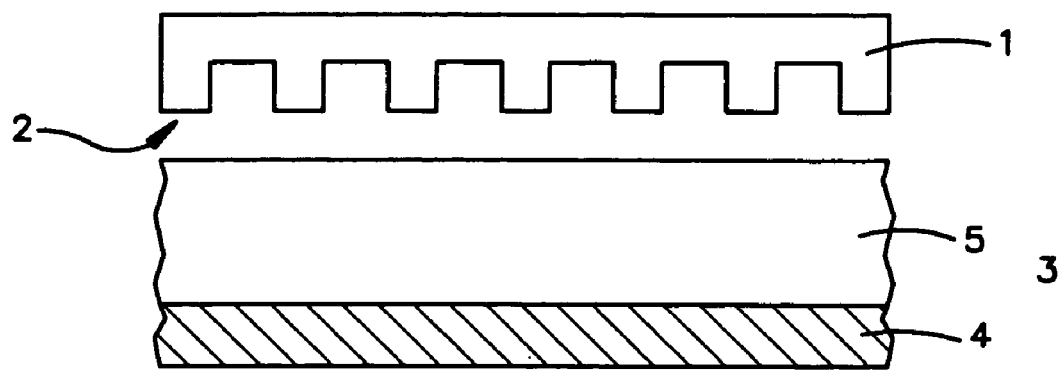

For clarity of disclosure, and not by way of limitation, the detailed description of the invention is divided into the subsections which follow.

5. DETAILED DESCRIPTION OF THE INVENTION

5.1 Product

The present invention relates to a medical device made by a method comprising providing a medical device that comprises a surface suitable for exposure to the body tissue, disposing a coating on at least a portion of the surface to form a first surface area, and imprinting an impression on at least a region of the coating to increase the first surface area. The coating may comprise a biologically active material. When the coated and imprinted medical device is in use, the biologically active material is released from the coating at a first rate that is different from a second rate, wherein the second rate is the rate of release of the same biologically active material from the coating had the impression not been imprinted on the coating. Likewise, the medical device, when in use, may be endothelialized to a body tissue at a first rate that is different from a second rate, wherein the second rate is the rate of endothelialization of the medical device to the body tissue had the impression not been imprinted on the coating.

The present invention also relates to a method of making a medical device, such as a stent, comprising providing a medical device that comprises a surface suitable for exposure to the body tissue, disposing a coating on at least a portion of the surface to form a first surface area, and imprinting an impression on at least a region of the coating to increase the first surface area.

One of the major benefits of this invention is the effect of the impression imprinted on the coating of the medical device on the endothelialization of the medical device to the surrounding body tissue. One of the concerns with drug-eluting medical devices, such as stents, is the effect that the drug has on device endothelialization. By increasing the rate of endothelialization, the restenosis rates in post-angioplasty patients or other patients undergoing similar procedures, may decrease. Since microscopic grooves can increase the migration rate of endothelial cells (see U.S. Pat. No. 6,190,404 to Palmaz et al.), the impression on the medical device coating can be used to increase endothelialization. In U.S. Pat. No. 6,190,404 to Palmaz et al. endothelialization is promoted by etching the inner wall of a stent. In contrast, the coated and printed stents comprise a coating imprinted with an impression on the coating surface, not the inner wall of the stent.

Another major benefit of this invention is that it also presents a cost-effective, reliable way to increase the surface area of the coating on the medical device. One of the major problems with current drug-eluting medical devices is the inability to effectively and reliably control the rate of drug elution. Using the methods of the inventor, drug release rates can be controlled by engineering surface morphology of the coating through imprinting. By manipulating the topology of the pattern on the coating, or by manipulating the concentration of a drug in the coating, different release rates can be achieved.

5.1.1 Medical Devices

Medical devices that are useful in the present invention can be made of any biocompatible material suitable for medical devices in general which include without limitation natural polymers, synthetic polymers, ceramics, and metallics. In one embodiment, the medical device is a composite of one or more of these materials. In certain embodiments, ceramic material is preferred. Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used. In certain other embodiments, metallic material (e.g., niobium, niobium-zirconium, and tantalum) is more preferable. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Metallic materials may be made into elongated members or wire-like elements and then woven to form a network of metal mesh. Polymer filaments may also be used together with the metallic elongated members or wire-like elements to form a network mesh. If the network is made of metal, the intersection may be welded, twisted, bent, glued, tied (with suture), heat sealed to one another, or connected in any manner known in the art.

The polymer(s) useful for forming the medical device should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly (dimethyl siloxane), polycyanoacrylates, polyphosphazenes, poly(amino acids), ethylene glycol I dimethacrylate, poly (methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly($\epsilon$-caprolactone), poly($\beta$-hydroxybutyrate), polydioxanone, poly($\gamma$-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., Arg-Gly-Asp (RGD), in which the polymers retain their structural integrity while allowing for attachment of molecules, such as proteins, nucleic acids, and the like.

The polymers may be dried to increase its mechanical strength. The polymers may then be used as the base material to form a whole or part of the medical device.

Furthermore, although the invention can be practiced by using a single type of polymer to form the medical device, various combinations of polymers can be employed. The appropriate mixture of polymers can be coordinated to produce desired effects when incorporated into a medical device.

In a specific embodiment, the medical device comprises a surface comprising a ceramic layer. Preferably, the ceramic layer extends the time period for releasing the material from the medical device.

The different forms of the biologically active material or polymer of the invention may be used to form a medical or prosthetic device, preferably a stent, which may be inserted or implanted into a blood vessel of a subject.

Examples of the medical devices suitable for the present invention include, but are not limited to, stents, surgical staples, catheters (e.g., central venous catheters and arterial catheters), guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units and plasmapheresis units.

Medical devices of the present invention include those that have a tubular or cylindrical-like portion. The tubular portion of the medical device need not to be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

In addition, the tubular portion of the medical device may be a sidewall that is comprised of a plurality of struts defining a plurality of openings. The struts may be arranged in any suitable configuration. Also, the struts do not all have to have the same shape or geometric configuration. Each individual strut has a surface adapted for exposure to the body tissue of the patient. The tubular sidewall may be a stent.

In certain embodiments of the present invention, the insertable or implantable portion of the medical device of the present invention has a surface. The surface may have a plurality of openings therein. Preferably, the medical device is a stent having a sidewall comprising a plurality of struts defining a plurality of openings. When the medical device is a stent comprising a plurality of struts, the surface is located on the struts.

The medical device may be formed after application of the coating or it may be pre-fabricated before application of the coating. The pre-fabricated medical device is in its final shape. For example, if the finished medical device is a stent having an opening in its sidewall, then the opening is formed in the device before application of the coating.

Medical devices which are particularly suitable for the present invention include any kind of stent for medical purposes which is known to the skilled artisan. In one embodiment, the medical device is an intravascular stent. The stent may be a metallic intravascular stent, or an intravascular stent made of stainless steel.

5.1.2 Coating

Single or multiple coating layers may be formed on the surface of the medical device. The coating may be formed by applying at least one coating by spraying, dipping, direct deposition, or a combination thereof, as described in Section 5.2.1 infra.

The coating layers may contain different materials, such as different polymers and/or different biologically active materials. Each coating layer may contain the same combinations of polymers, but in different amounts or in different forms. Similarly, each coating layer may contain the same biologically active material but in different amounts or in different forms. In a preferred embodiment, a first coating layer comprises a biologically active material, whereas a second coating layer is substantially free of the biologically active material.

For example, a first coating layer and a second or additional coating layer may contain different polymers that release certain biologically active materials or certain forms of the biologically active material at different rates. Also, the coating layers may be of different thicknesses and be arranged in any configuration on the medical device, such as disposed on different areas of the medical device. For example, the coating layers may be adjacent on the surface of the medical device. Alternatively, a first coating layer may be disposed on the surface of the medical device and a second or additional coating layer may be disposed over at least a portion of the first coating layer.

In a specific embodiment, the different coating layers comprise the same ratio of biologically active material(s) to polymer(s). In another specific embodiment, the different coating layers comprise different ratios of biologically active material(s) to polymer(s).

In specific embodiments, a coating comprises at least 5%, at least 10%, at least 20%, at least 30%, at least 40%, at least 50%, at least 60%, at least 70%, at least 80%, at least 90%, at least 95%, at least 97%, at least 99% or more by weight of a polymer. In specific embodiments, a coating comprises at least 5%, at least 10%, at least 20%, at least 30%, at least 40%, at least 50%, at least 60%, at least 70%, at least 80%, at least 90%, at least 95%, at least 97%, at least 99% or more by weight of a biologically active material.

In certain embodiments, the coating comprises different polymers at different amounts or different ratios. In specific embodiments, a coating comprises a first polymer and a second polymer at a ratio of about 90:10, 80:20, 70:30, 60:40, or 50:50.

In certain embodiments, the coating comprises different biologically active materials at different amounts or different ratios. In specific embodiments, a coating comprises a first and a second biologically active material at a ratio of about 90:10, 80:20, 70:30, 60:40, or 50:50.

In certain embodiments, the coating is capable of providing sustained release of a biologically active material over a time period. In specific embodiments, the drug-eluting coating is capable of releasing about 5%, about 10%, about 15%, about 20%, about 30%, about 40%, about 50%, about 60%, about 70%, about 80%, about 90% or more of the biologically active material over a time period. The time period for release of the biologically active material from the coating ranges from about 30 minutes, about 1 hour, about 2 hours, about 3 hours, about 4 hours, about 5 hours, about 6 hours, about 12 hours, about 1 day, about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 1 year, about 2 years, or longer.

Coatings suitable for forming the coating of the medical devices of the present invention can include one or more biologically active materials as describe in Section 5.1.2.1 infra, or one or more polymers as described in Section 5.1.2.2 infra.

5.1.2.1 Biologically Active Material

As used herein, the term "biologically active material" encompasses drugs, genetic materials, and biological materials. Non-limiting examples of suitable biologically active material include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), pimecrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti thrombin antibodies, anti platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifinctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, taxol, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In a preferred embodiment, the therapeutic agent is taxol (e.g., Taxol®), or its analogs or derivatives. In another preferred embodiment, the therapeutic agent is paclitaxel (i.e., paclitaxel, an analog of paclitaxel, a derivative of paclitaxel, or a combination thereof). In yet another preferred embodiment, the therapeutic agent is an antibiotic such as erythromycin, amphotericin, rapamycin, adriamycin, etc.

As used herein, the term "genetic materials" means DNA or RNA, including, without limitation, of DNA/RNA encoding a useful protein stated below, intended to be inserted into a human body including viral vectors and non-viral vectors.

As used herein, the term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic biologically active materials include, but are not limited to:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;

anti-inflammatory agents such as glucocorticoids, betamethasone, dexamethasone, prednisolone, corticosterone, budesonide, estrogen, sulfasalazine, rosiglitazone, mycophenolic acid and mesalamine;

anti-neoplastic/anti-proliferative/anti-miotic agents such as paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, taxol and its analogs or derivatives;

anesthetic agents such as lidocaine, bupivacaine, and ropivacaine;

anti-coagulants such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin, macrolides such as rapamycin (sirolimus) and everolimuns;

angiogenic substances, such as acidic and basic fibroblast growth factors, estrogen including estradiol (E2), estriol (E3) and 17-beta estradiol; and drugs for heart failure, such as digoxin, beta-blockers, angiotensin-converting enzyme (ACE) inhibitors including captopril and enalopril, statins and related compounds.

Preferred biologically active materials include anti-proliferative drugs such as steroids, vitamins, and restenosis-inhibiting agents. Preferred restenosis-inhibiting agents include microtubule stabilizing agents such as Taxol® (i.e., paclitaxel, an analog of paclitaxel, a derivative of paclitaxel, or a combination thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred biologically active materials include nitroglycerin, nitrous oxides, nitric oxides, antibiotics, aspirins, digitalis, estrogen derivatives such as estradiol and glycosides.

In one embodiment, the biologically active material promotes healing by inhibiting cell proliferation, contraction, migration, or hyperactivity. In another embodiment, the biologically active material promotes healing by inhibiting the activity of smooth muscle cells.

In a certain embodiment, the biologically active material is an immunosuppressant, an antiproliferative agent, or a combination thereof. In a preferred embodiment, the biologically active material is an immunosuppressant such as, but not limited to sirolimus, everolimus, tacrolimus, or a combination thereof. In another preferred embodiment, the biologically active material is an antiproliferative agent such as, but not limited to paclitaxel.

5.1.2.2 Polymer

As used herein, the term "polymer" is used interchangeably with the terms "polymer material" and "polymeric matrix".

The polymer suitable for use in the preparation of the drug-eluting coatings of the present invention should be a material that is biocompatible and avoids irritation to body tissue. Preferably, the polymer used in the coatings of the present invention are selected from the following: polyurethanes, silicones (e.g., polysiloxanes and substituted polysiloxanes), and polyesters. Also preferable as a polymeric material is copolymers of styrene and isobutylene, or more preferably, styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as poly(lactide-co-glycolide) (PLGA), polyvinyl alcohol (PVA), poly(L-lactide) (PLLA), polyanhydrides, polyphosphazenes, polycaprolactone (PCL), polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid (PLA), polyglycolic acid (PGA), polyethylene oxide (PEO), polylactic acid-polyethylene oxide copolymers, EPDM (etylene-propylene-diene) rubbers, fluorosilicones, polyethylene glycol (PEG), polyalkylene glycol (PAG), polysaccharides, phospholipids, and combinations of the foregoing.

In certain embodiments, the polymer is hydrophilic (e.g., PVA, PLLA, PLGA, PEG, and PAG). In certain other embodiments, the polymer is hydrophobic (e.g., PLA, PGA, polyanhydrides, polyphosphazenes, PCL, copolymers of styrene and isobutylene, and polyorthoesters).

More preferably for medical devices which undergo mechanical challenges, e.g., expansion and contraction, the polymer should be selected from elastomeric polymers such as silicones (e.g., polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating is capable of undergoing deformation under the yield point when the device is subjected to forces, stress or mechanical challenge.

The polymer may be biodegradable or biostable. In preferred embodiments, the polymer is biodegradable. Biodegradable polymeric materials can degrade as a result of hydrolysis of the polymer chains into biologically acceptable, and progressively smaller compounds. In one embodiment, a polymeric material comprises polylactides, polyglycolides, or their co-polymers. Polylactides, polyglycolides, and their co-polymers break down to lactic acid and glycolic acid, which enters the Kreb's cycle and are further broken down into carbon dioxide and water.

Biodegradable solids may have differing modes of degradation. On one hand, degradation by bulk erosion/hydrolysis occurs when water penetrates the entire structure and degrades the entire structure simultaneously, i.e., the polymer degrades in a fairly uniform manner throughout the structure. On the other hand, degradation by surface erosion occurs when degradation begins from the exterior with little/no water penetration into the bulk of the structure (see, e.g., Gopferich A. Mechanisms of polymer degradation and erosion. Biomaterials 1996; 17(103):243-259, which is incorporated by reference herein in its entirety). For some novel degradable polymers, most notably the polyanhydrides and polyorthoesters, the degradation occurs only at the surface of the polymer, resulting in a release rate that is proportional to the surface area of the drug delivery system. Hydrophilic polymeric materials such as PLGA will erode in a bulk fashion. Various commercially available PLGA may be used in the preparation of the coatings. For example, poly(d,l-lactic-co-glycolic acid) are commercially available. A preferred commercially available product is a 50:50 poly (D,L) lactic co-glycolic acid having a mole percent composition of 50% lactide and 50% glycolide. Other suitable commercially available products are 65:35 DL, 75:25 DL, 85:15 DL and poly(d,l-lactic acid) (d,l-PLA). For example, poly(lactide-co-glycolides) are also commercially available from Boehringer Ingelheim (Germany) under its Resomer©, e.g., PLGA 50:50 (Resomer RG 502), PLGA 75:25 (Resomer RG 728) and d,l-PLA (resomer RG 206), and from Birmingham Polymers (Birmingham, Ala.). These copolymers are available in a wide range of molecular weights and ratios of lactic to glycolic acid.

In one embodiment, the coating comprises copolymers with desirable hydrophilic/hydrophobic interactions (see, e.g., U.S. Pat. No. 6,007,845 to Domb et al., which describes nanoparticles and microparticles of non-linear hydrophilic-hydrophobic multiblock copolymers, which is incorporated by reference herein in its entirety). In a specific embodiment, the coating comprises ABA triblock copolymers consisting of biodegradable A blocks from PLG and hydrophilic B blocks from PEO.

5.1.2.3 Solvent

To prepare the coating, the constituents, i.e., polymers, biologically active material, and additional components, are suspended and/or dissolved in a solvent.

One or more solvents may be used to prepare the coating. In one embodiment, the solvents used to prepare a coating include ones which can dissolve the polymeric material into solution or suspend the polymeric material. Any solvent which does not alter or adversely impact the therapeutic properties of the biologically active material can be employed.

The solvent in the coating can comprise one or more of the following solvents: tetrahydrofuran, chloroform, toluene, acetone, isooctane, 1,1,1-trichloroethane, or a mixture thereof. In addition to the solvent the polymer that is used in the coating can be styrene-isobutylene-styrene, polyurethanes, silicones, polyesters, polyolefins, polyisobutylene, ethylene-alphaolefin copolymers, acrylic polymers and copolymers, vinyl halide polymers, polyvinyl ethers, polyvinylidene halides, polyacrylonitrile, polyvinyl ketones, polyvinyl aromatics, polyvinyl esters, copolymers of vinyl monomers, copolymers of vinyl monomers and olefins, polyamides, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM rubbers, fluorosilicones, polyethylene glycol, polysaccharides, phospholipids, or a combination thereof.

5.1.3 Patterns 5.1.3.1 Different Sizes, Shapes, and Uniformity

As used herein, the terms "pattern" and "impression" are interchangeable.

By imprinting the coating with different patterns, drug release rates can be controlled. Depending on the method used in imprinting a pattern, the resulting impression will have a different size and shape. In certain embodiments, soft lithography, or photolithography techniques can be used to imprint nanoscale impressions on the coating.

Figure 1B:
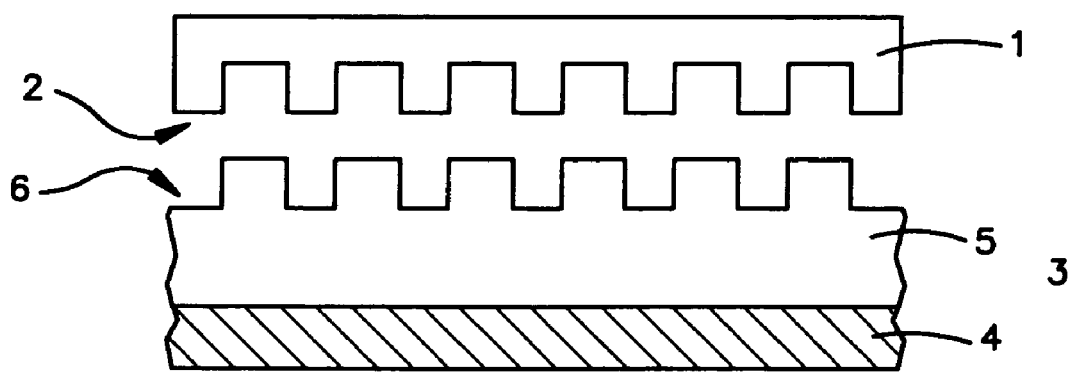

The impression may be printed over the entire coating of the medical device or over only certain regions of the coating on the medical device. In one embodiment, multiple techniques may be used to imprint multiple impressions on a single device. In one embodiment of the present invention, impressions are imprinted on a coated medical device using a dimethylsiloxane (PDMS) mold with a pattern. As shown in FIGS. 1A and 1B, a PDMS mold 1 having a pattern 2 can be used to imprint impressions 6 on a coated medical device 3 having a surface 4 and a coating 5 disposed on at least a portion of the surface 4. FIG. 1A shows a coated medical device 3 before its coating 5 is imprinted with a PDMS mold 1. FIG. 1B shows the coated medical device 3 after its coating 5 is imprinted with impressions 6 by the PDMS mold 1.

The impression imprinted on the coating may be uniform or random. In one embodiment, the impression is uniformly printed on one section of the coating and randomly imprinted on another section of the coating. In another embodiment, the impression is uniformly imprinted over the entire coating. In another embodiment, the impression is randomly imprinted on the entire coating.

The device may be imprinted with any shaped impression. The pattern may be smooth, without sharp edges or corners. The impression may include deep or shallow grooves. In one embodiment, the impression is orthogonal. The impression may be comprised of polygons such as circles, triangles, squares, shapes with regular or irregular sides and angles, or a combination thereof. In another embodiment, the impression comprises three-dimensional polygons.

5.1.3.2 Increases Surface Area

The surface morphology of the device can be engineered to target a specific location of the body or in order to regulate the rate at which a biologically active material is released into the body. For example, in one embodiment, the pattern is only applied to a first portion of the medical device. This type of imprinting pattern increases the surface area of the first portion. This embodiment improves the localization of drug delivery by increasing the rate of drug release into the lumen while maintaining the same drug release rate in the blood.

Manipulating surface morphology allows for drug release rates on the ends of the medical device to be the same as the drug release rates in the middle of the medical device. In one embodiment, densely grooved patterns are imprinted in the middle of the device while more loosely grooved patterns are imprinted on the ends of the device. Since the edge of a device has more surface area over a given length than a face of the device, this imprinting pattern keeps the drug release rate constant.

By imprinting a coating multiple times with different impressions, a very wide variety of surface areas can be achieved. The types of topology on a given region of the coating can be doubled by stamping the coating an additional time. An example of imprinting a coating with different impressions is shown in FIGS. 2A and 2B.

Figure 2A:
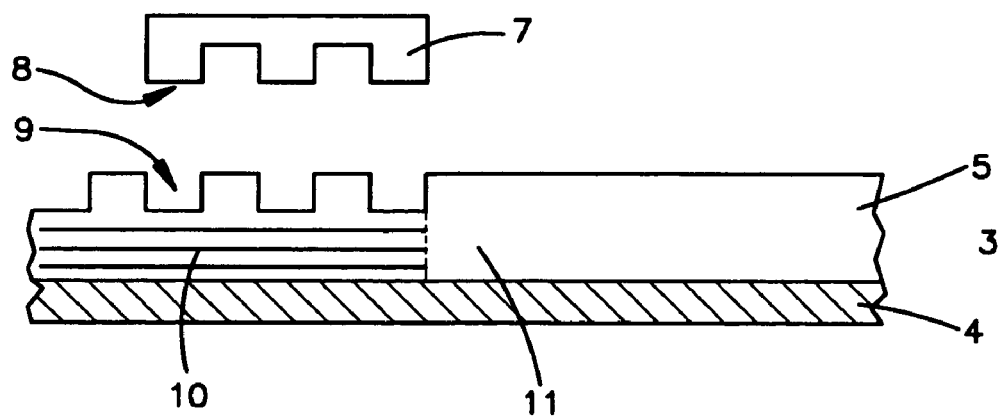
FIG. 2A is a partial cross-sectional view of a second exemplary coated medical device having a coating comprising impressions imprinted with a single elastomeric stamp.

FIG. 2A shows a coated medical device 3 having a surface 4 and a coating 5 disposed on a portion of the surface 4. The coating 5 is imprinted with a first elastomeric stamp 7. The first elastomeric stamp 7 has a pattern 8, which in this instance comprises convex square shapes, that leaves a first type of impression, which is a square concave impression 9 on the coating 5. After the impression 9 is imprinted, the coating 5 has two regions: a first region 10 that includes the square concave impression 9 and a second region 11 that is not impressed.

Figure 2B:
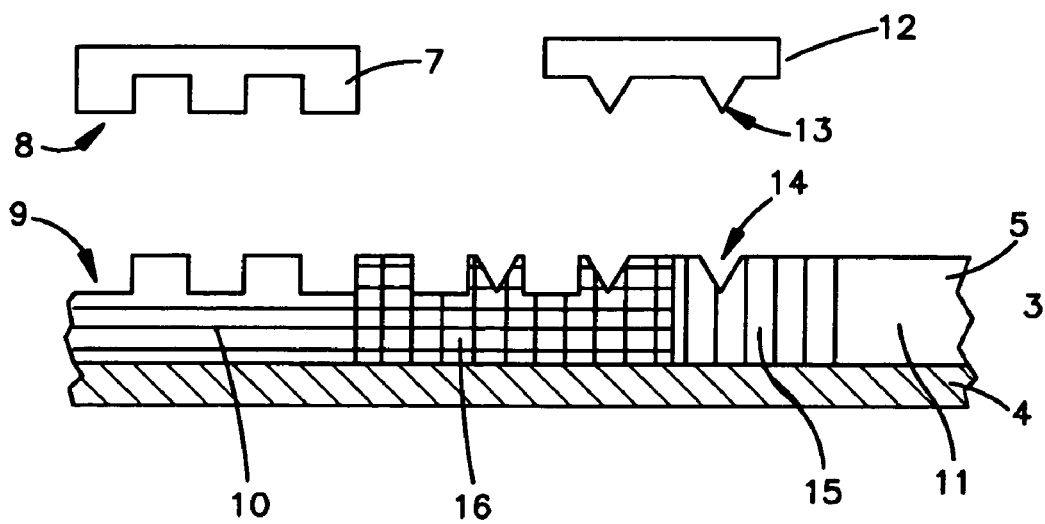
FIG. 2B is a partial cross-sectional view of a third exemplary coated medical device having a coating comprising impressions imprinted with two elastomeric stamps.

FIG. 2B shows a coated medical device 3 wherein the coating 5 has been impressed with both the first elastomeric stamp 7 and a second elastomeric stamp 12. The square convex pattern 8 from the first elastomeric stamp 7 leaves a square concave impression 9. The triangular convex pattern 13 from the second elastomeric stamp 12 leaves a triangular concave pattern 14. After the coating 6 has been impressed with both stamps, the coating 5 has four regions: a first region 10 impressed with the first elastomeric stamp 7, a second region 15 impressed with the second elastomeric stamp 12, a third region 16 impressed with both the first elastomeric stamp 7 and the second elastomeric stamp 12, and a fourth region 11 that is not impressed. In other embodiments other types of impressions can be used and also an additional number of impressions can be used.

5.1.3.3 Increases Endothelialization

Preferably, the pattern of the impression is not random. In one embodiment, a repetitive geometric pattern that matches with cell biology may be used so that the impression promotes cell growth. In another embodiment, the pattern imprinted on the coating of the medical device allows for increased rates of migration of endothelial cells post-implantation of the device.

In a preferred embodiment, the medical device is endothelialized to the body tissue at a first rate that is different from a second rate, wherein the second rate is the rate of endothelialization of the medical device to the body tissue had the impression not been imprinted on the coating.

In one embodiment, the release rate of a biologically active material from a medical device having an imprinted coating is greater than the release rate of the same biologically active material from a medical device having a non-imprinted coating. In another embodiment, the release rate of a biologically active material from a medical device having an imprinted coating is slower than the release rate of the same biologically active material from a medical device having a non-imprinted coating.

5.2 Method for Making Coated and Imprinted Medical Device

In the present invention, the medical device is made by a method comprising a medical device with a surface suitable for exposure to the body tissue, disposing a coating on at least a portion of the surface to form a first surface area, and imprinting an impression on at least a region of the coating in order to increase the first surface area.

5.2.1 Methods of Applying Coatings to Medical Device

In the present invention, one or more coatings comprising a biologically active material as described in Section 5.1.2.1 supra or a polymer described in Section 5.1.2.2 supra, or a combination thereof, may be applied by any method to a surface of a medical device to form a coating. Examples of suitable methods of applying coating to a medical device include, but are not limited to, spraying, dipping, or direct deposition. In one embodiment of the present invention, more than one coating method can be used to coat a medical device.

Furthermore, before applying the coating, the surface of the medical device is optionally subjected to a pre-treatment, such as roughening, oxidizing, sputtering, plasma-deposition or priming in embodiments where the surface to be coated does not comprise depressions. Sputtering is a deposition of atoms on the surface by removing the atom from the cathode by positive ion bombardment through a gas discharge. Also, exposing the surface of the device to a primer is a possible method of pre-treatment.

5.2.2 Methods of Imprinting Patterns on Coating

In the present invention there are multiple ways to imprint an impression on the coating of the medical device. These methods include, but are not limited to, microcontact printing, inkjet printing, screen printing, replica molding, microtransfer molding, micromolding in capillaries, solvent-assisted micromolding, proximal probe lithography, photolithography, scanning probe lithography, and embossing techniques. In one embodiment of the present invention, more than one imprinting method can be used to coat a medical device.

The pattern may be imprinted, but is not limited to being imprinted, using a flat platten, a stamp, rollers, a mandrel with a pattern, a balloon with a pattern that is imprinted as the balloon is inflated, or a combination thereof. The balloon and mandrel techniques are useful for imprinting on the inside of a medical device such as, but not limited to, a stent.

5.2.2.1 Printing Techniques

After a medical device has been coated, an impression may be imprinted onto the coating by a printing technique. This printing technique may include, but is not limited to, microcontact printing, inkjet printing, screen printing, or a combination thereof.

The microcontact printing method may use a polydimethylsiloxane (PDMS) or other elastomeric stamp to print the pattern. In one embodiment, the desired pattern can be created on the stamp using conventional photolithography or another lithography technique. In another embodiment, microcontact printing is used to contemporaneously pattern every surface of the medical device that is in contact with the stamp at a given time.

Once the stamp is made, the pattern can be transferred to the coated medical device surface. By pressing the stamp into the coating before the coating is fully dry, the pattern on the stamp is imprinted onto the coating. Preferably, the coating is not dried when the stamp is impressed into the coating. In one embodiment, the coating may be 70% to 100% dry when the stamp is imprinted onto the coating. In another embodiment, the coating may have rheological properties which enable the pattern to be retained on the coating while the coating is still malleable enough to be imprinted.

5.2.2.2 Molding Techniques

After a medical device has been coated, an impression may be imprinted onto the coating by a molding technique. This molding technique may include, but is not limited to, replica molding, microtransfer molding, micromolding in capillaries, solvent-assisted micromolding, or a combination thereof.

The molding technique may use a polydimethylsiloxane (PDMS) or other elastomeric stamp to mold the pattern. In one embodiment, replica molding may be used to efficiently duplicate the information such as shape, morphology, and structure present on the surface of the coating. In another embodiment, replica molding may be used for duplicating two or three dimensional topolgies on the coating of a medical device in a single step. Preferably, replica molding may enable the duplication of complex structures in the stamp in multiple copies of the coating with nanoscale resolution in a simple, reliable and inexpensive way. A single implementation of replica molding may be used multiple times on a single medical device, for a single time on the coatings of multiple medical devices, or for a combination thereof.

The size and shape of the stamp may be manipulated by controlled deformation of the stamp used to mold the pattern. By mechanically stretching, bending, compressing, or a combination thereof, the surface of the stamp and thereby the pattern on the coating, can be inexpensively and reliably altered.

Microtransfer molding may be used to pattern a large surface of the medical device coating over a short period of time. In one embodiment, the coating of a medical device is molded with interconnected and isolated microstructures using microtransfer molding. In another embodiment, microtransfer molding is used in fabricating patterns where the coating of a medical device is nonplanar.

In one embodiment of the invention, microtransfer molding is used to make impressions of arrays of parallel lines on the coating of a medical device. In another embodiment of the invention, geometric patterns that enhance endothelialization is imprinted on the device through microtransfer molding.

Micromolding in capillaries may also be used to imprint an impression on a medical device coating. In one embodiment of the invention, micromolding in capillaries is used to form nanoscale patterns on a medical device coating in a single step. In another embodiment of the invention micromolding in capillaries is used to create a freestanding microstructure out of the medical device coating, comprised of two interconnected layers, with an independent relief structure in each.

Solvent-assisted micromolding may be used to pattern the coating on a medical device in a single step. An elastomeric stamp, such as one fabricated with PDMS may be used. In one embodiment of the invention, solvent-assisted micromolding is used to create quasi-three-dimensional structures that are well defined and clearly resolved.

5.2.2.3 Lithography Techniques

Patterns may be imprinted on a medical device coating using lithography techniques. This lithography technique may include, but is not limited to, proximal probe lithography, scanning probe lithography, photolithography, or a combination thereof.

In one embodiment of the invention, scanning probe lithography is used for patterning the medical device coating with features smaller than 100 nm, 50 nm, 10 nm, 1 nm, or less. In one embodiment, scanning probe lithography is used to pattern the medical device coating with mechanical patterning such as scratching, nanoindentaion, or local heating with a sharp tip. In another embodiment, the pattern is imprinted on the coating using dip-pen nanolithography techniques.

5.2.2.4 Embossing Techniques

Embossing techniques may be used for imprinting impressions on the coating of a medical device. Through recent advances in embossing, even nanoscale patterns can be imprinted through the embossing technique. In one embodiment of the invention, the embossing technique is used to add a pattern to a coating that is too dried to be imprinted using either scanning probe lithography or printing techniques.

5.2.3 Method of Using Medical Device

The invention relates generally to the therapeutic use of the coated medical devices made by the processes of Section 5.2 supra to address conditions such as stenosis and restenosis. Medical devices comprising a biologically active material as described in Section 5.1.2.1 supra or a polymer described in Section 5.1.2.2 supra, or both, can be inserted or implanted into a subject in need thereof.

In certain embodiments, the biologically active material may be used to inhibit the proliferation, contraction, migration and/or hyperactivity of cells of the brain, neck, eye, mouth, throat, esophagus, chest, bone, ligament, cartilage, tendons, lung, colon, rectum, stomach, prostate, breast, ovaries, fallopian tubes, uterus, cervix, testicles or other reproductive organs, hair follicles, skin, diaphragm, thyroid, blood, muscles, bone, bone marrow, heart, lymph nodes, blood vessels, arteries, capillaries, large intestine, small intestine, kidney, liver, pancreas, brain, spinal cord, and the central nervous system. In a preferred embodiment, the biologically active material is useful for inhibiting the proliferation, contraction, migration and/or hyperactivity of muscle cells, e.g., smooth muscle cells.

In certain other embodiments, the biologically active material may be used to inhibit the proliferation, contraction, migration and/or hyperactivity of cells in body tissues, e.g., epithelial tissue, connective tissue, muscle tissue, and nerve tissue. Epithelial tissue covers or lines all body surfaces inside or outside the body. Examples of epithelial tissue include, but are not limited to, the skin, epithelium, dermis, and the mucosa and serosa that line the body cavity and internal organs, such as the heart, lung, liver, kidney, intestines, bladder, uterine, etc. Connective tissue is the most abundant and widely distributed of all tissues. Examples of connective tissue include, but are not limited to, vascular tissue (e.g., arteries, veins, capillaries), blood (e.g., red blood cells, platelets, white blood cells), lymph, fat, fibers, cartilage, ligaments, tendon, bone, teeth, omentum, peritoneum, mesentery, meniscus, conjunctiva, dura mater, umbilical cord, etc. Muscle tissue accounts for nearly one-third of the total body weight and consists of three distinct subtypes: striated (skeletal) muscle, smooth (visceral) muscle, and cardiac muscle. Examples of muscle tissue include, but are not limited to, myocardium (heart muscle), skeletal, intestinal wall, etc. The fourth primary type of tissue is nerve tissue. Nerve tissue is found in the brain, spinal cord, and accompanying nerve. Nerve tissue is composed of specialized cells called neurons (nerve cells) and neuroglial or glial cells.

The biologically active material, drug-eluting coatings, and coated medical devices of the present invention may also be used to treat diseases that may benefit from decreased cell proliferation, contraction, migration and/or hyperactivity, including, but not limited to stenosis and restenosis.

In particular, the biologically active material, such as paclitaxel, may be used to treat or prevent diseases or conditions that may benefit from decreased or slowed cell proliferation, contraction, migration or hyperactivity. In specific embodiments, the present invention inhibits or reduces at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, at least 10%, at least 5%, or at least 1% of cell proliferation, contraction, migration and/or hyperactivity.

The present invention further provides methods for treating or preventing stenosis or restenosis. In particular, the invention relates to methods for treating or preventing stenosis or restenosis by inserting or implanting a coated medical device of the invention into a subject.

As used herein, the terms "subject" and "patient" are used interchangeably. The subject can be an animal, preferably a mammal including a non-primate (e.g., a cow, pig, horse, cat, dog, rat, and mouse) and a primate (e.g., a monkey, such as a cynomolgous monkey, chimpanzee, and a human), and most preferably a human.

In one embodiment, the subject can be a subject who had undergone a regimen of treatment (e.g., percutaneous transluminal coronary angioplasty (PTCA), also known as balloon angioplasty, and coronary artery bypass graft (CABG) operation).

The therapeutically effective amount of a biologically active material for the subject will vary with the subject treated and the biologically active material itself. The therapeutically effective amount will also vary with the condition to be treated and the severity of the condition to be treated. The dose, and perhaps the dose frequency, can also vary according to the age, gender, body weight, and response of the individual subject. As used herein, the term "therapeutically effective amount" refers to that amount of the biologically active material sufficient to inhibit cell proliferation, contraction, migration, hyperactivity, or address other conditions (e.g., cancer). A therapeutically effective amount may refer to the amount of biologically active material sufficient to delay or minimize the onset of symptoms associated with cell proliferation, contraction, migration, hyperactivity, or address other conditions. A therapeutically effective amount may also refer to the amount of the biologically active material that provides a therapeutic benefit in the treatment or management of certain conditions such as stenosis or restenosis and/or the symptoms associated with stenosis or restenosis.

The present invention is useful alone or in combination with other treatment modalities. In certain embodiments, the subject can be receiving concurrently other therapies to treat or prevent stenosis or restenosis. In certain embodiments, the treatment of the present invention further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATH®I/H, Smart MI95, LYMPHOCIDE™, Smart I D10, ONCOLYM™, rituximab, gemtuzumab, or trastuzumab. In certain other embodiments, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

6. EXAMPLES

6.1 A Method of Making a Coated and Imprinted Medical Device

Using photolithography, create the desired pattern on a PDMS stamp. Take a medical device such as a metallic stent, dispose a coating onto the stent by dipping it into polyurethane. Before the coating is completely dry, use microcontact printing to imprint the pattern from the PDMS stamp onto the polyuethane coating. Let the coating completely dry.

What is claimed is:

1. A method of making a medical device comprising:
   providing a medical device that comprises a surface suitable for exposure to body tissue;
   disposing a coating on at least a portion of the surface to form a first surface area; and
   imprinting an impression on at least a region of the coating by a technique comprising microcontact printing, inkjet printing, or screen printing, wherein said impression increases the first surface area.

2. The method of claim 1, wherein the coating comprises a biologically active material.

3. The method of claim 2, wherein when the medical device is in use, the biologically active material is released from the coating at a first rate that is different from a second rate, wherein the second rate is the rate of release of the same biologically active material from the coating had the impression not been imprinted on the coating.

4. The method of claim 2, wherein the biologically active material inhibits cell proliferation, contraction, migration, or hyperactivity.

5. The method of claim 2, wherein the biologically active material inhibits an activity of smooth muscle cell.

6. The method of claim 2, wherein the biologically active material comprises an immunosuppressant or an antiproliferative agent.

7. The method of claim 6, wherein the immunosuppressant comprises sirolimus, pimecrolimus, everolimus, or tacrolimus.

8. The method of claim 6, wherein the antiproliferative agent comprises paclitaxel.

9. The method of claim 2, wherein the coating is capable of providing sustained release of the biologically active material over a period of time.

10. The method of claim 2, wherein the coating comprises a plurality of coating layers.

11. The method of claim 1, wherein when the medical device is in use, is endothelialized to the body tissue at a first rate that is different from a second rate, wherein the second rate is the rate of endothelialization of the medical device to the body tissue had the impression not been imprinted on the coating.

12. The method of claim 1, wherein the coating is formed by applying at least one coating composition by spraying, dipping, or direct deposition.

13. The method of claim 1, wherein the medical device is an intravascular stent.

14. The method of claim 13, wherein the intravascular stent is a metallic intravascular stent.

15. The method of claim 14, wherein the metallic intravascular stent is a stainless steel intravascular stent.

16. The method of claim 13, wherein the intravascular stent comprises a polymer.

17. The method of claim 1, wherein the coating further comprises a polymer.

18. The method of claim 17, wherein the polymer comprises styrene-isobutylene-styrene, polyurethanes, silicones, polyesters, polyolefins, polyisobutylene, ethylene-alphaolefin copolymers, acrylic polymers and copolymers, vinyl halide polymers, polyvinyl ethers, polyvinylidene halides, polyacrylonitrile, polyvinyl ketones, polyvinyl aromatics, polyvinyl esters, copolymers of vinyl monomers, copolymers of vinyl monomers and olefins, polyamides, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactid acid, polyglycolic acid, polylactic acid-polyethylene oxide copolymers, EPDM rubbers, fluorosilicones, polyethylene glycol, polysaccharides, or phospholipids.

* * * * *